(12) United States Patent
Shim (10) Patent No.: US 8,355,139 B2
(45) Date of Patent: Jan. 15, 2013

(54) SEMICONDUCTOR APPARATUS INCLUDING ALIGNMENT TOOL

(75) Inventor: Seong-Bo Shim, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 428 days.

(21) Appl. No.: 12/706,981

(22) Filed: Feb. 17, 2010

(65) Prior Publication Data

US 2010/0214569 A1  Aug. 26, 2010

(30) Foreign Application Priority Data

Feb. 26, 2009 (KR) .................. 10-2009-0016414

(51) Int. Cl.
*G01B 11/02* (2006.01)
(52) U.S. Cl. ........................................ 356/508
(58) Field of Classification Search ............ 356/490, 356/508–510, 399–400
See application file for complete search history.

(56) References Cited

U.S. PATENT DOCUMENTS

| 6,034,378 | A  | * | 3/2000 | Shiraishi | 250/559.29 |
| 6,628,390 | B1 | * | 9/2003 | Johnson | 356/400 |
| 6,937,334 | B2 | * | 8/2005 | Monshouwer et al. | 356/399 |
| 7,002,667 | B2 | * | 2/2006 | Levasier et al. | 355/69 |

FOREIGN PATENT DOCUMENTS

| JP | 64-089325 | 4/1989 |
| JP | 07-120939 | 5/1995 |
| KR | 10-0158681 | 8/1998 |
| KR | 10-1998-0065731 | 10/1998 |

* cited by examiner

*Primary Examiner* — Michael A Lyons
(74) *Attorney, Agent, or Firm* — Myers Bigel Sibley & Sajovec, P.A.

(57) ABSTRACT

Provided is a semiconductor apparatus. The semiconductor apparatus includes a reference grating and a plurality of detectors. The reference grating diffracts an optical signal generated by being reflected from the alignment grating of a substrate to diffraction beams with different orders. The plurality of detectors measure intensities of a plurality of diffraction beams selected from the diffraction beams, respectively.

9 Claims, 7 Drawing Sheets

→ X-Axis Direction

Fig. 3B

→ X-Axis Direction

SEMICONDUCTOR APPARATUS INCLUDING ALIGNMENT TOOL

CROSS-REFERENCE TO RELATED APPLICATIONS

This U.S. non-provisional patent application claims priority under 35 U.S.C. §119 of Korean Patent Application No. 10-2009-0016414, filed on Feb. 26, 2009, the entire contents of which are hereby incorporated by reference.

BACKGROUND

The present disclosure herein relates generally to semiconductor devices, and more particularly, to semiconductor device manufacturing.

Semiconductor devices have various advantages such as miniaturization, multi-function, and low manufacturing costs. However, with high-integration of semiconductor devices, various limitations may occur. These limitations may make it difficult to manufacture semiconductor devices with desired characteristics and performance.

An alignment process may be required during semiconductor manufacturing. For example, an alignment process may be required in a photolithography process for defining semiconductor patterns for semiconductor devices, a test process for testing operational characteristics of semiconductor devices, and/or a defect detection process for checking defects of semiconductor devices. When misalignment occurs in a semiconductor device, characteristics of the semiconductor device may be degraded, and/or operation states of the semiconductor device may be affected. With high-integration of semiconductor devices, critical dimensions and/or distances of semiconductor patterns formed on a semiconductor device are becoming increasingly smaller. For example, semiconductor devices having very fine semiconductor patterns with critical dimensions of several nanometers may be required. As a result, alignment margins for semiconductor manufacturing may gradually decrease. To increase the alignment margins of semiconductor manufacturing, various research efforts are ongoing.

SUMMARY

Embodiments of the present invention provide semiconductor apparatus with an optimized alignment states that facilitate high-integration.

Embodiments of the present invention also provide a semiconductor apparatus that very precisely aligns a substrate.

Embodiments of the present invention also provide a semiconductor apparatus that realizes a very precise alignment and includes an alignment tool having a simplified structure.

Embodiments of the present invention provide semiconductor apparatuses including: a stage on which a substrate including an alignment grating is loaded, the stage being horizontally movable in one direction; a reference grating diffracting an optical signal generated by being reflected from the alignment grating to diffraction beams with different orders; and a plurality of detectors measuring intensities of a plurality of diffraction beams selected from the diffraction beams, respectively.

In some embodiments, the intensities of the selected diffraction beams measured by the detectors may be changed according to the horizontal movement of the stage. The semiconductor apparatuses may further include a controller detecting a position of the stage at which the measured intensities of the selected diffraction beams are maximized all together. The measured intensities of each of the selected diffraction beams according to the horizontal movement of the stage may be a maximum value. In some embodiments, at least two among the maximum values may be different from each other.

In some embodiments, a duty ratio of the reference grating may be the same as a duty ratio of the alignment grating.

In some embodiments, the semiconductor apparatuses may further include an image lens unit disposed between the reference grating and the stage. The image lens unit may transmit an image of the alignment grating to the reference grating. The optical signal generated by the alignment grating may include the image of the alignment grating transmitted by the image lens unit.

In some embodiments, a period of the reference grating may be equal to a value of multiplying a magnification of the image lens unit by a period of the alignment grating.

In some embodiments, the semiconductor apparatuses may further include a Fourier transform lens unit disposed between the reference grating and the detectors, the Fourier transform lens unit transforming progressing directions of the generated diffraction beams into directions parallel to each other.

In some embodiments, the reference grating may have a duty ratio of about 50%, and the selected diffraction beams have odd orders.

In some embodiments, a distance between the reference grating and the detectors may be in a range of about $10^5$ times to about $10^7$ times of a period of the reference grating.

BRIEF DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the figures.

DETAILED DESCRIPTION OF THE EMBODIMENTS

The present invention is described more fully hereinafter with reference to the accompanying drawings, in which example embodiments of the invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to," "coupled to" or "responsive to" another element or layer, it can be directly on, connected, coupled or responsive to the other element or layer or intervening elements or layers may be present. In contrast, when an element is referred to as being "directly on," "directly connected to," "directly coupled to" or "directly responsive to" another element or layer, there are no intervening elements or layers present. Like numbers refer to like elements throughout. As used herein, the term "and/or" includes any and all combinations (mixtures) of one or more of the associated listed items and may be abbreviated as "/".

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The structure and/or the device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the present invention are described herein with reference to cross-section illustrations that are schematic illustrations of idealized embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

It should also be noted that in some alternate implementations, the functionality of a given block may be separated into multiple blocks and/or the functionality of two or more blocks may be at least partially integrated.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present application, and will not be interpreted in an idealized or overly formal sense unless expressly so defined herein.

Figure 1:
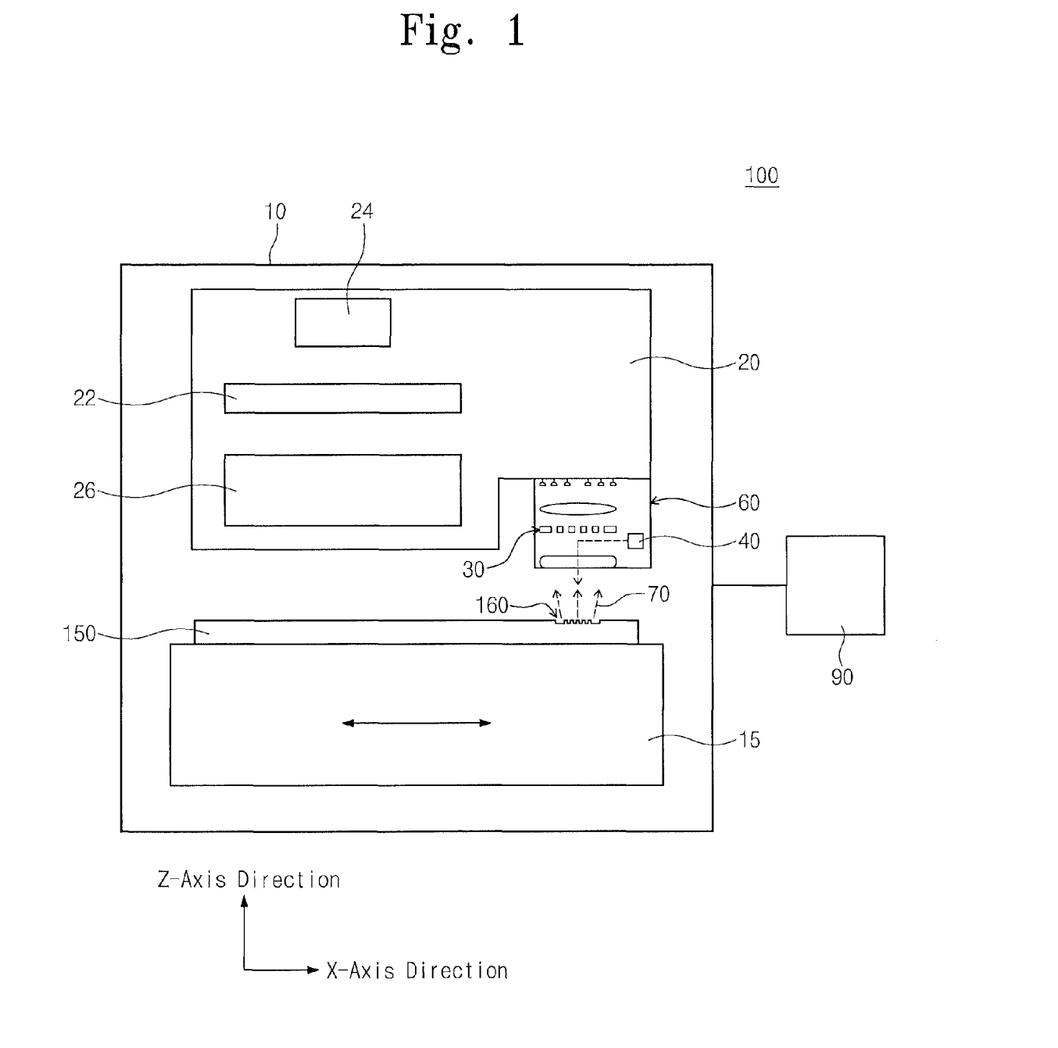
FIG. 1 is a view of a semiconductor apparatus according to an embodiment of the inventive concept.
Figure 2:
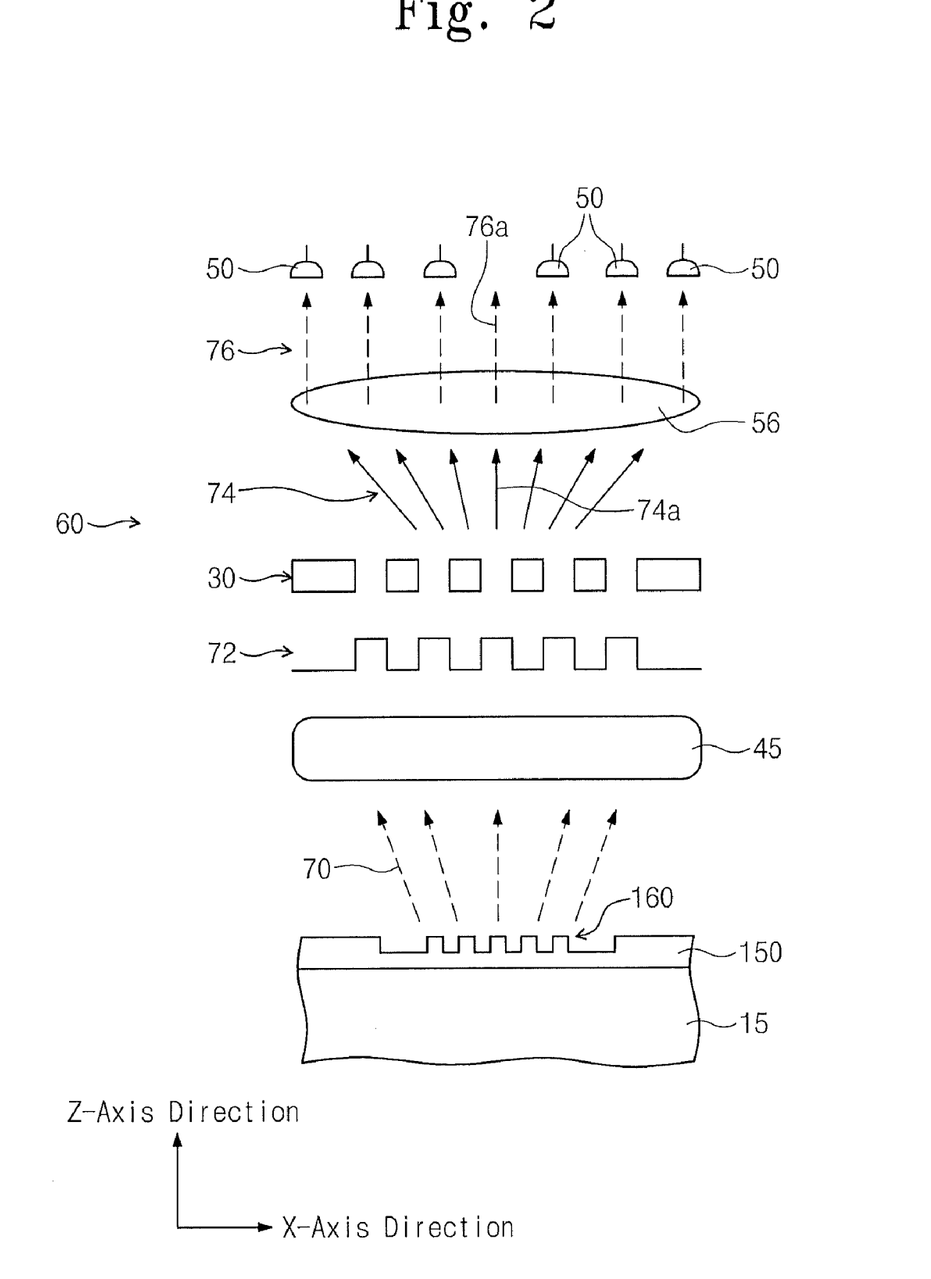
FIG. 2 is an enlarged view illustrating an alignment tool and a semiconductor substrate of FIG. 1.
Figure 3A:
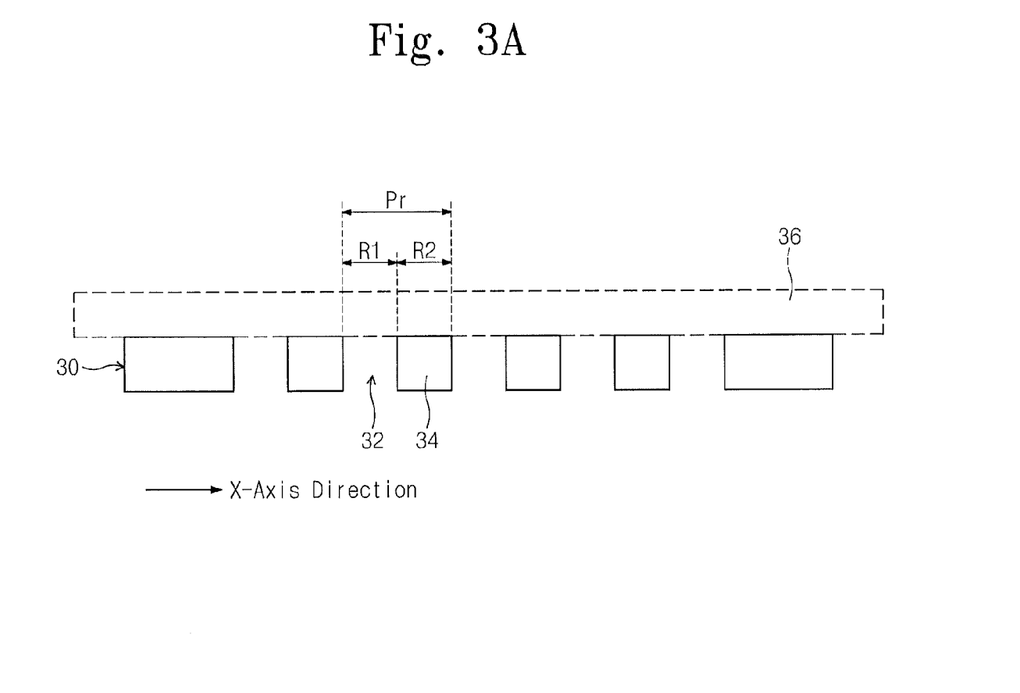
FIG. 3A is an enlarged view illustrating a reference grating of FIG. 1.
Figure 3B:
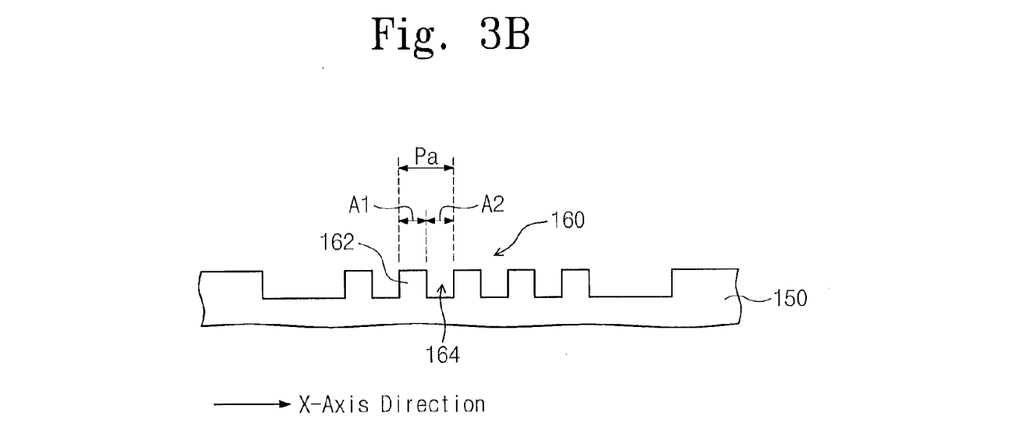
FIG. 3B is an enlarged view illustrating an alignment grating of FIG. 1.

FIG. 1 is a view of a semiconductor apparatus according to an embodiment of the present invention, and FIG. 2 is an enlarged view illustrating an alignment tool and a semiconductor substrate of FIG. 1. FIG. 3A is an enlarged view illustrating a reference grating of FIG. 1, and FIG. 3B is an enlarged view illustrating an alignment grating of FIG. 1.

Referring to FIG. 1, a semiconductor apparatus 100 may include a body 10 in which semiconductor processes are performed and a controller 90 connected to the body 10. The body 10 may include a stage 15 on which a substrate 150 is loaded. The stage 15 may be horizontally movable in one direction. The one direction may be an x-axis direction as illustrated in FIG. 1. In addition, the stage 15 may be horizontally movable in another direction perpendicular to the one direction. The other direction may be a y-axis direction (not shown). That is, the stage 15 may be reciprocally movable in two directions, such as the x-axis and y-axis directions. Also, the stage 15 may be moved in a z-axis direction perpendicular to the x-axis and the y-axis directions, as illustrated in FIG. 1. The substrate 150 may include a semiconductor substrate (e.g., a wafer) on which a semiconductor device is formed. The substrate 150 includes an alignment grating 160.

An alignment tool 60 may be disposed above the stage 15. The alignment tool 60 is spaced from the stage 15. In addition, the alignment tool 60 may be spaced also from the loaded substrate 150. The alignment tool 60 may be mounted on a processing part 20. The alignment tool 60 and the processing part 20 may be fixed to each other. The processing part 20 may perform semiconductor manufacturing processes. For example, the processing part 20 may perform an exposure process. When the processing part 20 performs an exposure process, the processing part 20 may include a photomask (or reticle) 22. The photomask 22 may be detachable from the processing part 20. In addition, the processing part 20 may further include an exposure source 24 disposed above the photomask 22 and an exposure lens unit 26 disposed below the photomask 22. When the processing part 20 performs an exposure process, the semiconductor apparatus 100 may include a stepper-type exposure apparatus or a scanner-type exposure apparatus. However, embodiments of the present invention are not limited thereto. The processing part 20 may perform the other semiconductor processes in which alignment of semiconductor devices are required. For example, the processing part 20 may perform a test process for testing operational characteristics of semiconductor devices or a defect detection process for detecting positions of defects (hard defects or soft defects) of semiconductor devices.

The alignment tool 60 may include an alignment light source 40. The alignment light source 40 may irradiate light for aligning onto the alignment grating 160 of the substrate 150, and then the irradiated light may be reflected by the alignment grating 160. An image 70 of the alignment grating 160 may be generated by the light reflected from the alignment grating 160 and inputted into the alignment tool 60. FIG. 2 illustrates an enlarged view of the alignment tool 60 of FIG. 1. The alignment tool 60 will be described in detail with reference to FIG. 2.

Referring to FIGS. 1 and 2, the alignment tool 60 includes a reference grating 30 disposed above the stage 15. The reference grating 30 may be disposed above the alignment grating 160. The reference grating 30 diffracts an optical signal generated from the alignment grating 160 to diffraction beams 74 with different orders. The light irradiated by the alignment light source 40 may be reflected by the alignment grating 160 of the substrate, and then the optical signal may be generated by the light reflected from the alignment grating 160. The diffraction beams 74 include a zero-order diffraction beam 74a. The orders of the diffraction beams 74 disposed at one side of the zero-order diffraction beam 74a may have negative integer values, and the order of the diffraction beams disposed at the other side of the zero-order diffraction beam 74a may have positive integer values. Positions of the diffraction beams 74 having the negative integer orders may be symmetrical to those of the diffraction beams having the positive integer orders with respect to the zero-order diffraction beam 74a. As a diffraction beam may be far away from the zero-order diffraction beam 74a, an absolute value of an order of the diffraction beam may increase. A diffraction beam having a relatively lower absolute value of the order may have an intensity greater than that of a diffraction beam having a relatively higher absolute value of the order.

The alignment tool 60 may further include a plurality of detectors 50 for respectively measuring intensities of a plurality of diffraction beams selected from the diffraction beams 74. The detectors 50 may be disposed above the reference grating 30. The detectors 50 may be arranged in the one direction (for example, x-axis direction of FIG. 2). The detectors 50 may have substantially the same height. The selected diffraction beams 74 may be diffraction beams generated by a constructive interference. At least two diffraction beams of the selected diffraction beams 74 may have maximum intensities different from each other. As shown in FIG. 2, the selected diffraction beams 74 may not include the zero-order diffraction beam 74a. However, embodiments of the present invention are not limited thereto. The selected diffraction beams may include the zero-order diffraction beam 74a. Each of the detectors 50 may include an image sensor including a photodiode. For example, the detectors 50 may include charge coupled device (CCD) image sensors or complementary metal-oxide-semiconductor (CMOS) image sensors.

The alignment tool 60 may further include an image lens unit 45 disposed between the reference grating 30 and the stage 15. The image lens unit 45 may be disposed above the alignment grating 160 of the substrate 150. That is, the image lens unit 45 may be disposed between the reference grating 30 and the alignment grating 160. The image lens unit 45 may enlarge or reduce the image 70 of the alignment grating 160.

The image lens unit 45 may have a specific magnification. An image 72 of the alignment grating 160 passing through the image lens unit 45 may travel to the reference grating 30. The image lens unit 45 may include a compound lens in which a plurality of lenses are joined to each other.

The alignment tool 60 may further include a Fourier transform lens unit 56 disposed between the reference grating 30 and the detectors 50. The diffraction beams 74 separated by the reference grating 30 may progress in directions different from each other. The Fourier transform lens unit 56 transforms the progressing directions of the separated diffraction beams 74 into directions parallel to each other. That is, the diffraction beams 74 passing through the Fourier transform lens unit 56 may progress parallel to each other. However, since the diffraction beams 74 have the progressing directions different from each other, progressing paths of diffraction beams 76 passing through the Fourier transform lens unit 56 are spaced apart from each other. That is, the progressing paths of the diffraction beams 76 are parallel to and spaced apart from each other. A progressing path of a zero-order diffraction beam 76a passing through the Fourier transform lens unit 56 may be equal to that of the zero-order diffraction beam 74a generated by the reference grating 30. The diffraction beams 76 passing through the Fourier transform lens unit 56 may progress parallel to the z-axis direction. The diffraction beams 76 having the progressing directions parallel to each other may travel to the detectors 50 having substantially the same height, respectively. Due to the Fourier transform lens unit 56, a distance between the detectors 50 and the reference grating 30 can be reduced.

The Fourier transform lens unit 56 has large alignment tolerance with respect to the progressing directions of the diffraction beams 74. Also, the diffraction beams 76 passing through the Fourier transform lens unit 56 progress parallel to each other. Thus, alignment tolerance with respect to the z-axis direction of the detectors 50 increases. The Fourier transform lens unit 56 may include one lens. Alternatively, the Fourier transform lens unit 56 may include a compound lens in which a plurality of lenses are joined to each other.

FIGS. 3A and 3B illustrate enlarged views of the reference grating 30 and the alignment granting 160 of the substrate 150, respectively. The reference grating 30 and the alignment grating 160 will be described in detail with reference to FIGS. 3A and 3B.

Reference to FIGS. 2 and 3A, the reference grating 30 includes openings 32 and light shields 34. The opening 32 and light shields 34 may be alternately arranged along the one direction (the x-axis direction of FIG. 2) in the reference grating 30. Each of the openings 32 may have a slit shape. Thus, each of the light shields 34 may have a bar shape. The reference grating 30 has a period Pr in the one direction. The period Pr of the reference grating 30 may be equal to a sum of a width R1 of the opening 32 and a width R2 of the light shield 34 in the one direction. The openings 32 may be arranged to be equally spaced with respect to each other in the one direction. That is, the light shields 34 may have the same width R2 to each other. The openings 32 may be formed in a light shielding plate to form the reference grating 30. In this case, the openings 32 pass through the light shielding plate, and a portion of the light shield plate between a pair of the openings 32 adjacent to each other may correspond to the light shield 34. According to an embodiment of the present invention, the reference grating 30 may be attached to a surface of a transparent substrate 36.

Referring to FIGS. 2 and 3B, the alignment grating 160 may have a convexo-concave shape. That is, the alignment grating 160 may include protrusions 162 and recessions 164.

The protrusions 162 and the recessions 164 are alternately arranged in the one direction (the x-axis direction of FIG. 2). A period Pa of the alignment grating 160 in the one direction may be equal to a sum of a width A1 of the protrusion 162 and a width A2 of the recession 164 in the one direction. The protrusions 162 may have the same width A1 to each other, and also, the recessions 164 may have the same width A2 to each other.

Referring to FIGS. 2, 3A and 3B, the period Pr of the reference grating 30 may be equal to a value multiplying a magnification of the image lens unit 45 by the period Pa of the alignment grating 160. The reference grating 30 may have a duty ratio, also the alignment grating 160 may have a duty ratio. The duty ratios of the reference grating 30 and the alignment grating 160 may be expressed as following Equation 1.

Duty ratio (%) of reference grating 30=width $R1$ of opening 32/period $Pr \times 100$ Duty ratio (%) of alignment grating 160=width $R1$ of protrusion 162/period $Pa \times 100$   [Equation 1]

The duty ratio of the reference grating 30 may be equal to that of the alignment grating 160. The reference grating 30 may have a duty ratio of about 50%. When the reference grating 30 has the duty ratio of about 50%, the width R1 of the opening 32 may be substantially equal to the width R2 of the light shield 34. Also, when the reference grating 30 has the duty ratio of about 50%, the selected diffraction beams measured by the detectors 50 may have odd orders. However, embodiments of the present invention are not limited thereto. The reference grating 30 may have a duty ratio less or greater than about 50%. In this case, the alignment grating 160 and the reference grating 30 may have the same duty ratio.

Referring to FIGS. 1 and 2, as the stage 15 is horizontally moved in the one direction, the intensities of the selected diffraction beams measured by the detectors 50 may be changed. The intensities of the selected diffraction beams measured by the detectors 50 may be detected by the controller 90. Also, the controller 90 may detect a position change of the stage 15 according to changes of the intensities of the selected diffraction beams measured by the detectors 50.

The alignment tool 60 may allow the substrate 150 aligned with the stage 15 to be aligned along the one direction (for example, the x-axis direction of FIG. 2). The semiconductor apparatus 100 may further include a second alignment tool (not shown) allowing the stage 15 to be horizontally aligned along the other direction perpendicular to the one direction. The second alignment tool may include the same components as the alignment tool 60. However, openings and light shields of a reference grating of the second alignment tool may be alternately arranged in the other direction perpendicular to the one direction. In this case, the substrate 150 may further include a second alignment grating including protrusions and recessions, which are alternately arranged in the other direction perpendicular to the one direction.

According to an embodiment of the present invention, the alignment tool 60 may be a fine alignment tool in which the substrate 150 and the processing part 20 are aligned within one period Pa of the alignment grating 160. In this case, the semiconductor apparatus 100 may further include an additional alignment unit to align the substrate 150 and the processing part 20 into the period Pa of the alignment grating 160.

An alignment method of the above-described semiconductor apparatus 100 will be described with reference to FIGS. 4 and 5.

Figure 4:
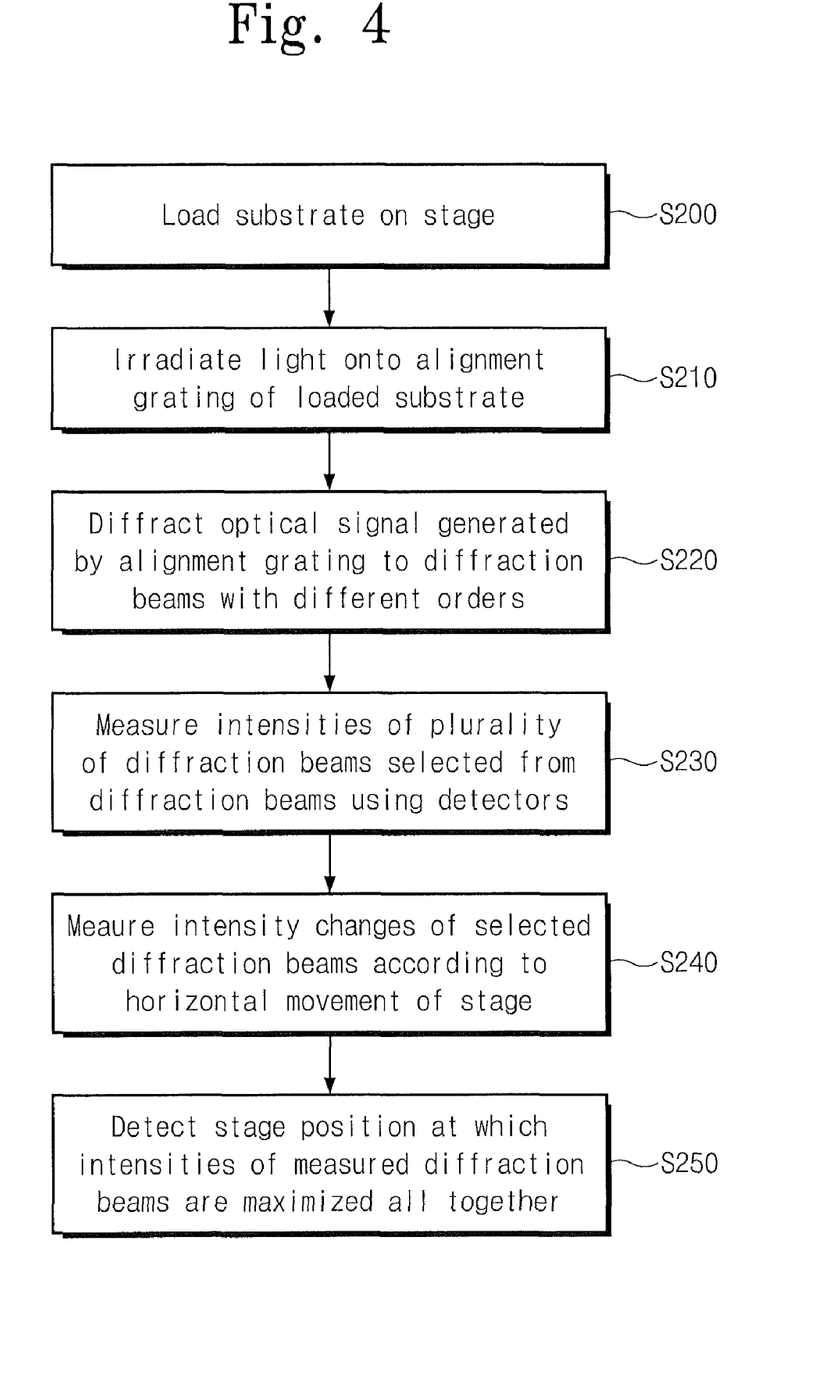
FIG. 4 is a flowchart of alignment method operations according to embodiments of the present invention.
Figure 5:
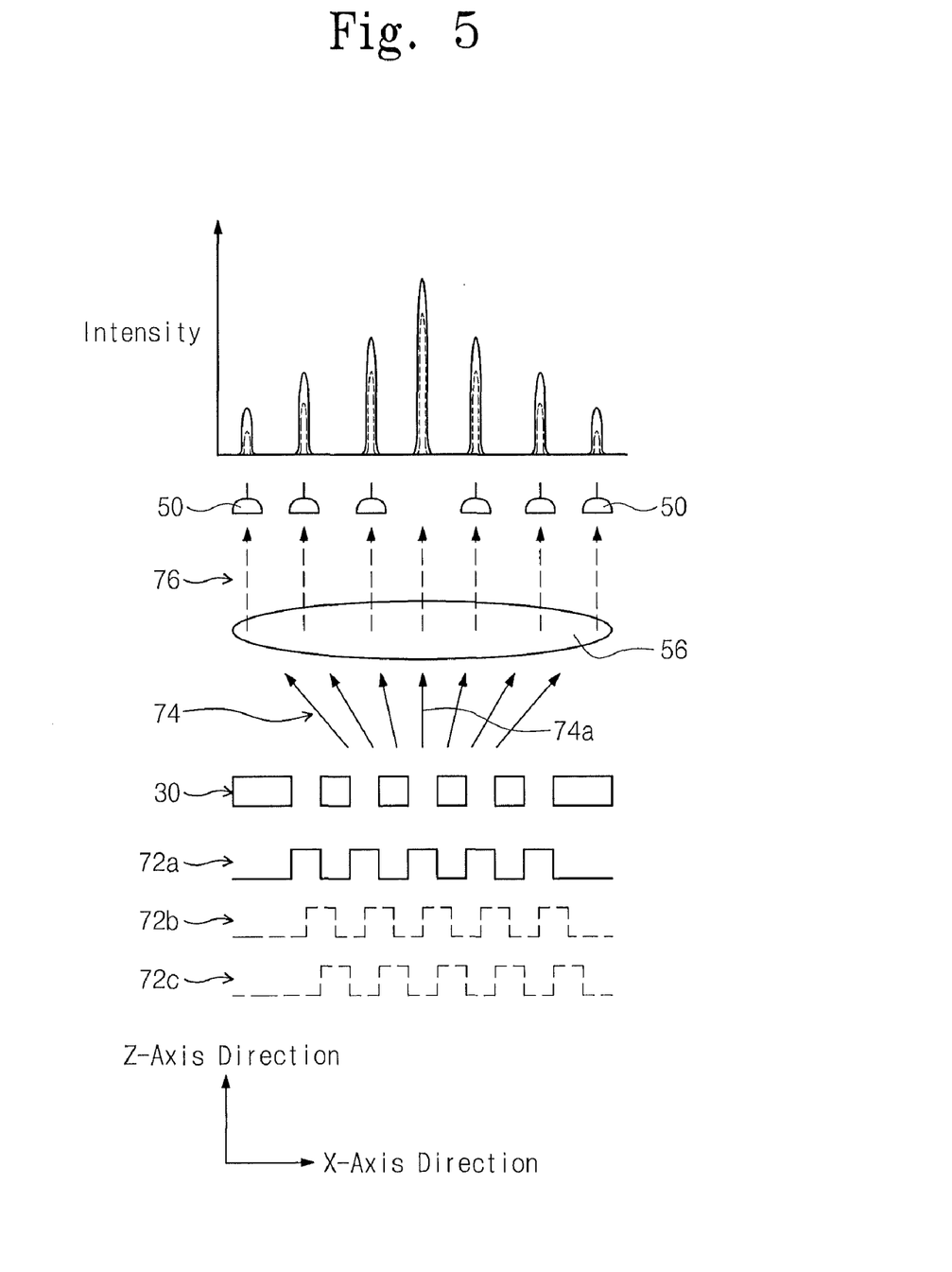
FIG. 5 is a view illustrating image changes of the reference grating and the alignment grating according to a horizontal movement of a stage to explain the alignment method of the semiconductor apparatus according to embodiments of the present invention.

FIG. 4 is a flowchart for explaining an alignment method of the semiconductor apparatus according to an embodiment of the present invention, and FIG. 5 is a view illustrating image changes of the reference grating and the alignment grating according to a horizontal movement of a stage to explain the alignment method of the semiconductor apparatus according to embodiments of the present invention.

Referring to FIGS. 1, 2, 3A, 3B, and 4, the substrate 150 including the alignment grating 160 is loaded on the stage 15 of the semiconductor apparatus 100 (S200). The substrate 150 may include a wafer for manufacturing semiconductor devices. Alternatively, the substrate 150 may include a wafer including manufactured semiconductor devices. The stage 15 may be horizontally moved to perform a pre-alignment process. The alignment grating 160 may be disposed below the alignment tool 60 through the pre-alignment process. According to the pre-alignment process, the loaded substrate 150 and the processing part 20 may be aligned into the period Pa of the alignment grating 160.

A light is irradiated onto the alignment grating 160 of the loaded substrate 150 (S210). The light of the alignment light source 40 included in the alignment tool 60 may be irradiated onto the alignment grating 160. A direction of the light of the alignment light source 40 may be changed by various mirrors, and then, may be irradiated onto the alignment grating 160. As shown in FIG. 2, the light of the alignment light source 40 may be irradiated onto the alignment grating 160 via the image lens unit 45. However, embodiments of the present invention are not limited thereto. The light of the alignment light source 40 may be irradiated onto the alignment grating 160 through a different path.

The reference grating 30 diffracts the optical signal generated by the alignment grating 160 to the diffraction beams 74 with different orders (S220). The light irradiated by the alignment light source 40 may be reflected by the alignment grating 160 to generate the image 70 of the alignment grating 160. The image 70 of the alignment grating 160 transmits the image lens unit 45 to move toward the reference grating 30. The image 72 of the alignment grating 160 passing through the image lens unit 45 may have a convexo-concave shape. Convex portions of the image 72 of the alignment grating 160 may be formed by being reflected by the protrusions 162 of the alignment grating 160, and concave portions of the image 72 of the alignment grating 160 may be formed by being reflected by the recessions 164 of the alignment grating 160. The convex portion of the image 72 may have an intensity greater than that of the concave portion of the image 72. The period Pr of the reference grating 30 may be equal to a value multiplying the magnification of the image lens unit 45 by the period Pa of the alignment grating 160. Thus, the image 72 of the alignment grating 160 passing through the image lens unit 45 may have the same period as the period Pr of the reference grating 30. Also, the reference grating 30 and the alignment grating 160 may have the same duty ratio. As a result, the image 72 of the alignment grating 160 passing through the image lens unit 45 may have the same duty ratio as that of the reference grating 30. The image 72 of the alignment grating 160 passing through the image lens unit 45 may correspond to the optical signal. The image 72 of the alignment grating 160 passes through the reference grating 30, and then, is diffracted and interferes with each other. Therefore, the diffraction beams 74 with different orders may be generated. The diffraction beams 74 with different orders may progress in directions different from each other. Thus, the diffraction beams 74 with different orders may have progressing paths different from each other.

The plurality of detectors 50 measures the intensities of the plurality of diffraction beams selected from the diffraction beams 74 with different orders (S230). The diffraction beams 74 with different orders may pass through the Fourier transform lens unit 56. The diffraction beams 76 passing through the Fourier transform lens unit 56 may be parallel to each other. At this time, the progressing paths of the diffraction beams 76 may be spaced apart from each other. The detectors 50 are disposed in the progressing paths of the diffraction beams selected from the diffraction beams 76, respectively. Absolute values of orders of at least two diffraction beams among the selected diffraction beams may be different from each other. According to an embodiment of the present invention, when the reference grating 30 has the duty ratio of about 50%, the selected diffraction beams measured by the detectors 50 may have odd orders. For example, the selected diffraction beams may include a first-order diffraction beam, a third-order diffraction beam, a fifth-order diffraction beam, and/or a seventh-order diffraction beam. According to an embodiment of the inventive concept, the positive integer order diffraction beams and the negative integer order diffraction beams, which have the same absolute value of orders, may be defined as one diffraction beam group. The selected diffraction beams may include a plurality of diffraction beam groups. In this case, the controller 90 may designate an intensity of each of the diffraction beam groups as a value of a sum of the measured intensities of the diffraction beams in the each of the diffraction beam groups.

The intensities of the selected diffraction beams according to a horizontal movement of the stage 15 are measured (S240). As the stage 15 is horizontally moved in the one direction (for example, the x-axis direction of FIG. 2), the image 72 of the alignment grating 160 is moved. As a result, the intensities of the selected diffraction beams are changed. This will be described in detail with reference to FIG. 5.

Referring to FIGS. 1 and 5, FIG. 5 illustrates positions of the image of the alignment grating according to the movement of the stage 15. Reference numeral 72*a* represents a first image 72*a* of the alignment grating corresponding to the reference grating 30. That is, convex portions of the first image 72*a* of the alignment grating precisely overlap openings of the reference grating 30, and concave portions of the first image 72*a* of the alignment grating precisely overlap light shields of the reference grating 30. When the first image 72*a* of the alignment grating passes through the reference grating 30, the intensities of the selected diffraction beams may be maximized.

A second image 72*b* of the alignment grating 160 illustrated in FIG. 5 illustrates a case in which an image of the alignment grating 160 and the reference grating 30 are partially overlapped with each other, and a third image 72*c* of the alignment grating illustrated in FIG. 5 illustrates a case in which the an image of the alignment grating 160 and the reference grating 30 completely miss each other. For convenience of description, although the second and third images 72*b* and 72*c* are disposed below the first image 72*a*, the inventive concept is not limited thereto. For example, the second and third images 72*b* and 72*c* may be disposed at the same height as the first image 72*a*.

Convex portions of the second image 72*b* partially overlap openings of the reference grating 30. Thus, when the second image 72*b* passes through the reference grating 30, a portion of the convex portions of the second image 72*b* is intercepted by the light shields of the reference grating 30. As a result, a duty ratio of the second image 72*b* passing through the reference grating 30 is changed to change the intensity of each of the selected diffraction beams. Convex portions of the third image 72*c* precisely overlap the light shields of the reference grating 30. Thus, the intensities of the selected diffraction beams may become zero.

The changes of the intensities of the selected diffraction beams according to the horizontal movement of the stage 15 may be different from each other. For example, an intensity change amount of a diffraction beam having a relatively lower absolute value of the order may be less than that of a diffraction beam having a relatively higher absolute value of the order. That is, an intensity change amount of the first-order diffraction beam may be less than that of the third-order diffraction beam. The intensities of the selected diffraction beams according to the horizontal movement of the stage 15 may be changed by periods. The intensities of each the selected diffraction beams according to the horizontal movement of the stage 15 has a maximum value. At least two among the maximum values of the selected diffraction beams are different from each other. Also, periods of the intensity changes of the selected diffraction beams may be different from each other. For example, a period of the intensity change of the diffraction beam having the relatively lower absolute value of the order may be greater than that of the diffraction beam having the relatively higher absolute value of the order.

Referring to FIGS. 1, 2, 4, and 5, a stage position at which measured intensities of the diffraction beams are maximized all together is detected (S250). The controller 90 may detect the intensities measured by the detectors 50 as well as the position of the stage 15. Thus, the controller 90 may detect the stage position at which the measured intensities of the diffraction beams are maximized all together. The alignment grating 160 and the reference grating 30 are aligned with each other at the position (i.e., a position of the stage 15 at which the first image 72*a* is generated) of the stage 15 at which the measured intensities of the diffraction beams are maximized all together.

A simulation for confirming intensity changes of the selected diffraction beams and periods of the intensity changes and a position of the stage 15 according to the horizontal movement of the stage 15 was performed. This will be described in detail with reference to FIG. 6.

Figure 6:
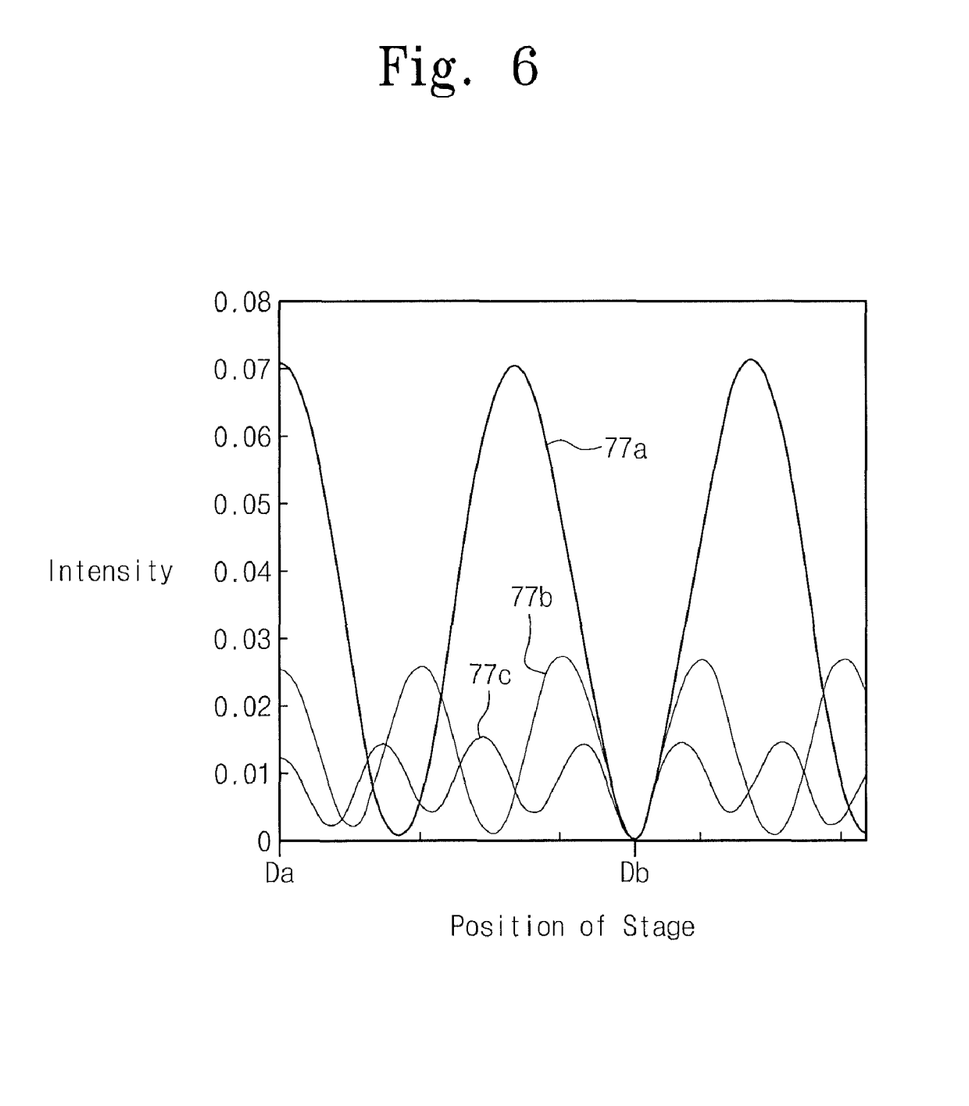
FIG. 6 is a simulation graph for explaining intensity changes of diffraction beams detected according to the horizontal movement of the stage of the apparatus of FIG. 1.

FIG. 6 is a simulation graph for explaining intensity changes of diffraction beams detected according to the horizontal movement of the stage 15.

Referring to FIGS. 1, 5 and 6, the reference grating 30 used for the simulation has a duty ratio of about 50%. The third-order diffraction beam, the fifth-order diffraction beam, and the seventh-order diffraction beam are used as the selected diffraction beams. In FIG. 6, an x-axis represents a position of the stage 15, and a y-axis represents intensities of diffraction beams. In FIG. 6, reference numeral 77*a* represents an intensity change of the third-order diffraction beam according to the horizontal movement (i.e., a horizontal movement of the image of the alignment grating) of the stage 15, and reference numeral 77*b* represents an intensity change of the fifth-order diffraction beam according to the horizontal movement (i.e., a horizontal movement of the image of the alignment grating) of the stage 15. Also, reference numeral 77*c* represents an intensity change of the seventh-order diffraction beam according to the horizontal movement of the stage 15.

As shown in FIG. 6, a maximum value of the intensity of the third-order diffraction beam 77*a* (i.e. low order diffraction beam) is greater than a maximum value of the intensity of the seventh-order diffraction beam 77*c* (i.e. high order diffraction beam). The intensity change of the third-order diffraction beam 77a is less than that of the seventh-order diffraction beam 77c, and the period of the third-order diffraction beam 77a is greater than that of the seventh-order diffraction beam 77c.

The substrate 150 and the alignment tool 60 are aligned with each other at a position Da of the stage 15 at which the intensities of the third-order, the fifth-order, and the seventh-order diffraction beams 77a, 77b, and 77c are maximized all together. The substrate 150 and the alignment tool 60 may be misaligned by half of the period of the alignment grating 160.

According to the above-described semiconductor apparatus 100 and the alignment method thereof, the substrate 150 is aligned using the diffraction beams generated by the reference grating 30. The diffraction beams selected from the diffraction beams include a diffraction beam having a high intensity change rate and a diffraction beam having a low intensity change rate according to the horizontal movement of the stage 15 on which the substrate is loaded. All of the intensity change rates of the selected diffraction beams are reflected to detect the position of the stage 15. As a result, the substrate 150 may be very precisely aligned.

Also, the alignment tool 60 including the reference grating 30 and the detectors 50 may have a very simplified structure. Thus, the alignment through the alignment tool 60 may be easily realized.

The alignment tool 60 may not include the Fourier transform lens unit 56. The other configuration of the alignment tool 60 will be described with reference to FIG. 7. Components equal to those illustrated in FIGS. 2, 3A, and 3B refer to like reference numerals in an alignment tool illustrated in FIG. 7.

Figure 7:
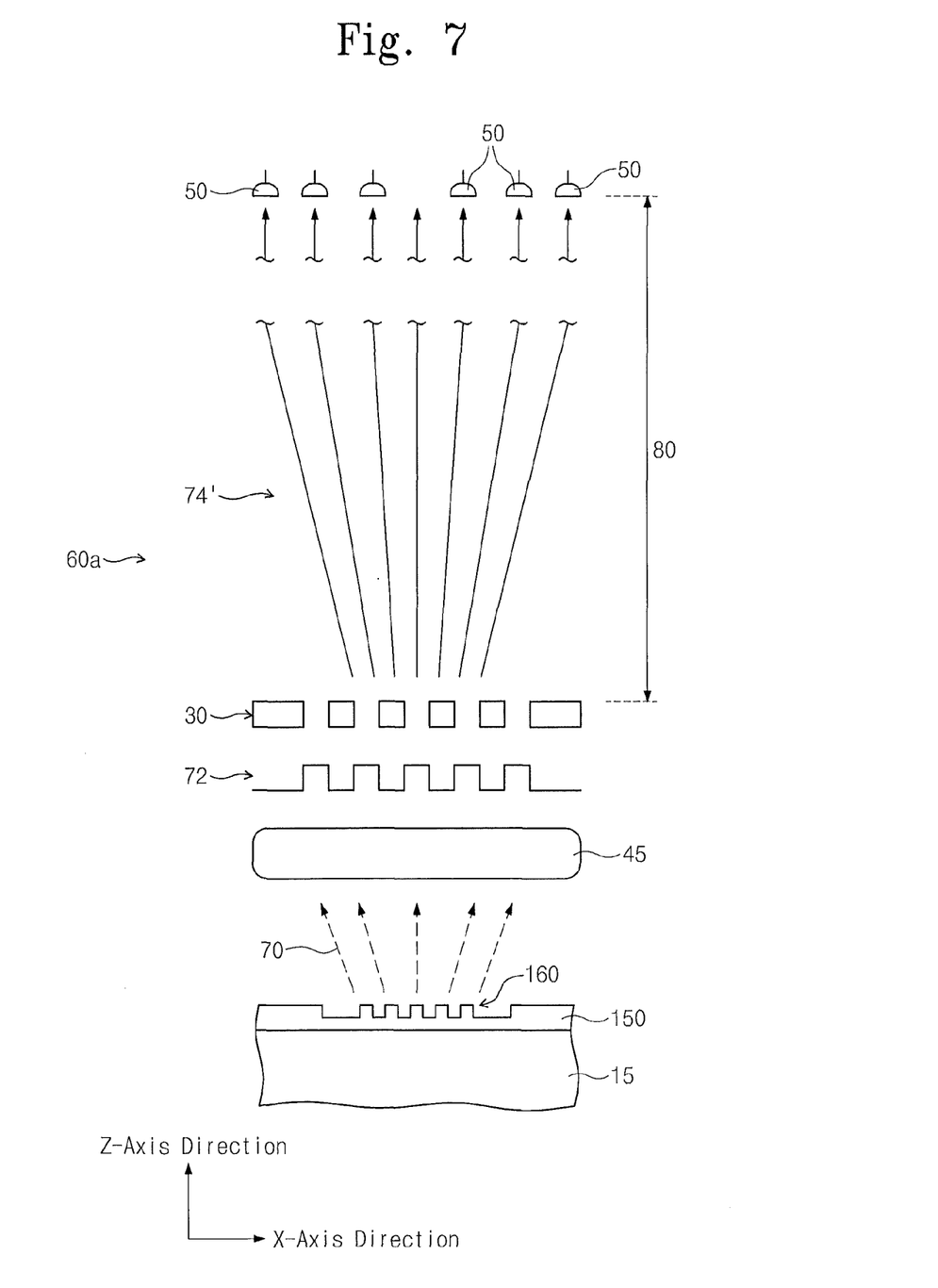
FIG. 7 is a view of an alignment tool included in a semiconductor apparatus according to another embodiment of the present invention.

FIG. 7 is a view of an alignment tool included in a semiconductor apparatus according to another embodiment of the present invention.

Referring to FIG. 7, an alignment tool 60a includes a reference grating 30 and detectors 50 spaced from the reference grating 30. A distance 80 between the reference grating 30 and the detectors 50 may be set to a distance in which diffraction beams 74' with different orders, which are generated by the reference grating 30, are substantially parallel to each other. Thus, diffraction beams selected from the diffraction beams 74' may be substantially parallel to each other and progress toward the respective detectors 50. The distance 80 between the reference grating 30 and the detectors 50 may be in a range of about $10^5$ times to about $10^7$ times of the period (See reference symbol Pr of the FIG. 3A) of the reference grating 30.

According to the alignment tool 60a of this embodiment, since the detectors 50 are sufficiently apart from the reference grating 30, the diffraction beams 74' may progress to the detectors 50 in a direction substantially parallel to each other. As a result, the alignment tool 60a may not require the Fourier transform lens unit 56 illustrated in FIG. 2. Therefore, the alignment tool 60a may have a less complex structure.

According to the above-described semiconductor apparatus, the reference grating may diffract the optical signal generated by being reflected by the alignment grating to the diffraction beams with different orders, and the detectors may detect the intensities of the plurality of diffraction beams selected from the diffraction beams, respectively. Since the substrate is aligned using the plurality of diffraction beams, very precise alignment may be realized. In addition, since the diffraction beams generated by the reference grating are used, the alignment tool having the further simplified structure may be provided. Also, due to the simplified structure of the alignment tool, stability of the alignment tool may be improved.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. A semiconductor apparatus comprising:
    a stage on which a substrate comprising an alignment grating is loaded, the stage being horizontally movable in one direction;
    a reference grating diffracting an optical signal generated by being reflected from the alignment grating to diffraction beams with different orders;
    a plurality of detectors measuring intensities of a plurality of diffraction beams selected from the diffraction beams, respectively, wherein the intensities of the selected diffraction beams measured by the detectors are changed according to a horizontal movement of the stage; and
    a controller detecting a position of the stage at which the measured intensities of the selected diffraction beams are maximized all together.

2. The semiconductor apparatus of claim 1, wherein the measured intensities of each of the selected diffraction beams according to the horizontal movement of the stage has a maximum value, and
    at least two among the maximum values are different from each other.

3. The semiconductor apparatus of claim 1, wherein a duty ratio of the reference grating is the same as a duty ratio of the alignment grating.

4. The semiconductor apparatus of claim 1, further comprising an image lens unit disposed between the reference grating and the stage, the image lens unit transmitting an image of the alignment grating to the reference grating,
    wherein the optical signal generated by the alignment grating comprises the image of the alignment grating transmitted by the image lens unit.

5. The semiconductor apparatus of claim 4, wherein a period of the reference grating is equal to a value multiplying a magnification of the image lens unit by a period of the alignment grating.

6. The semiconductor apparatus of claim 1, further comprising a Fourier transform lens unit disposed between the reference grating and the detectors, the Fourier transform lens unit transforming progressing directions of the generated diffraction beams into directions parallel to each other.

7. The semiconductor apparatus of claim 1, wherein the reference grating has a duty ratio of about 50%, and the selected diffraction beams have odd orders.

8. The semiconductor apparatus of claim 1, wherein a distance between the reference grating and the detectors is in a range of about $10^5$ times to about $10^7$ times of a period of the reference grating.

9. An apparatus, comprising:
    a stage movable in at least one direction and configured to receive a substrate having an alignment grating;
    a reference grating in adjacent, spaced-apart relationship with the stage, wherein the reference grating is configured to diffract an optical signal reflected from the alignment grating into a plurality of diffraction beams with different orders;

a plurality of detectors in adjacent, spaced-apart relationship with the reference grating and configured to measure intensities of selected ones of a plurality of diffraction beams, wherein movement of the stage changes the intensities of the selected diffraction beams; and a controller detecting a position of the stage at which the measured intensities of the selected diffraction beams are maximized all together.

* * * * *